United States Patent [19]

Mueller

[11] Patent Number: 4,559,337

[45] Date of Patent: Dec. 17, 1985

[54] 8-CHLORODIBENZ[B,F][1,4]OXAZEPINE-10(11H)-CARBOXYLIC ACID, 2-(ALKOXY-CONTAINING ACYL)HYDRAZIDES

[75] Inventor: Richard A. Mueller, Glencoe, Ill.

[73] Assignee: G.D. Searle & Co., Skokie, Ill.

[21] Appl. No.: 705,280

[22] Filed: Feb. 25, 1985

[51] Int. Cl.$^4$ .................. C07D 267/20; A61K 31/55
[52] U.S. Cl. .................................. 514/211; 260/330.7
[58] Field of Search ...................... 260/330.7; 514/211

[56] References Cited

U.S. PATENT DOCUMENTS

| | | | |
|---|---|---|---|
| 3,534,019 | 10/1970 | Coyne | 260/239 R |
| 3,917,649 | 11/1975 | Mueller | 260/330.7 |
| 3,989,719 | 11/1976 | Mueller | 260/330.7 |
| 3,992,375 | 11/1976 | Mueller | 260/330.7 |
| 4,045,442 | 8/1977 | Mueller | 260/244.4 |
| 4,125,532 | 11/1978 | Mueller | 260/244.4 |
| 4,170,593 | 10/1979 | Mueller | 260/243.3 |

OTHER PUBLICATIONS

J. H. Sanner, "Antagonism of Prostaglandin $E_2$ by 1-Acetyl-2-(8-Chloro-10,11-Dihydrodibenz[b,f][1,-4]Oxazepine-10-Carbonyl)Hydrazine (SC-19220)," Arch. Int. Pharmacodyn., 180, 46, (1969).

Primary Examiner—Norma S. Milestone
Attorney, Agent, or Firm—John J. McDonnell

[57] ABSTRACT

This invention relates to 8-chlorodibenz[b,f][1,4]-oxazepine-10(11H)-carboxylic acid, 2-(alkoxy-containing acyl)hydrazides that are useful as prostaglandin antagonists and analgesic agents.

17 Claims, No Drawings

8-CHLORODIBENZ[B,F][1,4]OXAZEPINE-10(11H)-CARBOXYLIC ACID, 2-(ALKOXY-CONTAINING ACYL)HYDRAZIDES

BACKGROUND OF THE INVENTION (a) Field of the Invention

This invention relates to 8-chlorodibenz[b,f][1,4]-oxazepine-10(11H)-carboxylic acid, 2-(alkoxy-containing acyl)hydrazides that are useful pharmacological agents. These compounds are prostaglandin antagonists having analgesic activity.

Analgesics are agents used in the treatment of pain and often are useful in alleviating inflammation. The major classes of analgesics include narcotic analgesics (or opiates) and analgesic-antipyretics such as the salicylates. Although the efficacy of opiates in relieving pain is well-established, the associated addiction liability is a distinct disadvantage. Although salicylate and salicylate-like agents (non-steroidal antiinflammatory agents) are also efficacious in relieving pain, they often exhibit undesirable side effects such as gastrointestinal irritation (as with aspirin), allergic response (as with aspirin), or liver toxicity with extended use (as with acetaminophen). The compounds included in this invention are neither opiates nor salicylates and may be expected not to exhibit the disadvantages of either class of compound.

(b) Prior Art

The closest prior art discloses compounds of the following formula wherein group B is carbonyl (CO) or sulfonyl ($SO_2$) and wherein A may be alkyl or substituted alkyl. The prior art does not, however, disclose the alkoxyalkyl or (alkoxy)alkoxyalkyl compounds of this invention.

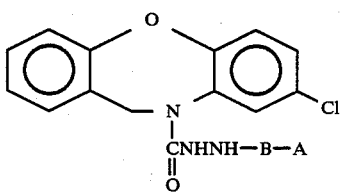

More specifically, U.S. Pat. No. 3,534,019 discloses compounds in which B and A together constitute "lower alkanoyl," and U.S. Pat. No. 3,989,719 discloses compounds in which B and A together constitute "higher alkanoyl." Thus, U.S. Pat. Nos. '019 and '719 each disclose compounds in which A is a hydrocarbon. The alkoxyalkyl or (alkoxy)alkoxyalkyl compounds of this invention are not disclosed.

U.S. Pat. Nos. 4,045,442, 4,125,532 (division of '442), and 4,170,593 (division of '532) disclose compounds in which B is carbonyl and A is (substituted amino)alkyl. The alkoxyalkyl or (alkoxy)alkoxyalkyl compounds of this invention are not disclosed.

U.S. Pat. Nos. 3,917,649 and 3,992,375 (division of '649) disclose compounds in which B is carbonyl or sulfonyl: where B is sulfonyl, A may be alkyl, haloalkyl, aryl, or aralkyl; and where B is carbonyl, A may be haloalkyl, alkenyl, or aryloxyalkyl. However, U.S. Pat. Nos. '649 and '375 do not disclose corresponding compounds in which A is alkoxyalkyl or (alkoxy)alkoxyalkyl. With respect to disclosure of the aryloxyalkyl compound, one skilled in the art will understand that steric, chemical, and other properties of aromatic ethers are distinguishable from those of alkyl ethers. Thus, the compounds of this invention are structurally distinct from the prior art.

SUMMARY OF THE INVENTION

This invention relates to compounds of Formula I:

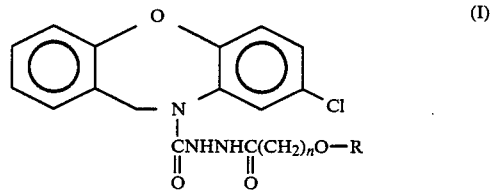

wherein R is:
(a) alkyl containing from 1 to 6 carbon atoms, inclusive; or
(b) alkoxyalkyl containing from 2 to 6 carbon atoms, inclusive; and wherein n is an integer of 1 to 4, inclusive.

Examples of alkyl of 1 to 6 carbon atoms, inclusive, are methyl, ethyl, propyl, butyl, pentyl, hexyl, and the isomeric forms thereof, generally referred to as lower alkyl.

Examples of alkoxyalkyl of 1 to 6 carbon atoms, inclusive, are methoxymethyl, 2-methoxyethyl, 3-methoxypropyl, 4-methoxybutyl, 5-methoxypentyl, ethoxymethyl, 2-ethoxyethyl, 3-ethoxypropyl, 4-ethoxybutyl, propoxymethyl, 2-propoxyethyl, 3-propoxypropyl, butoxymethyl, 2-butoxyethyl, pentoxymethyl, and the isometric forms thereof.

DESCRIPTION OF THE INVENTION

The compounds of this invention may be prepared by the method illustrated in Scheme A. Unless otherwise specified, the various substituents are defined as for Formula I, above.

SCHEME A

The compounds of this invention are prepared from 8-chloro-10,11-dihydrodibenz[b,f][1,4]oxazepine-10-carboxylic acid hydrazide (Formula II), the preparation of which is described in U.S. Pat. No. 3,534,019, by acylating with appropriate acyl halides of Formula III in the presence of a base. Preferred acylating conditions include reaction to the hydrazide (Formula II) and an acyl chloride (Formula III, X=Cl) in an unreactive organic solvent, such as dichloromethane, containing a tertiary amine, such as triethylamine. The acyl halides are readily available or may be prepared by methods well known to those skilled in the art, as illustrated in the Preparations below.

The preferred embodiment of this invention, as indicated by biological activity in the following assays, is a compound according to Formula I wherein R is butyl (exemplified in Example 1 below).

The compounds are prostaglandin $E_2$ antagonists, as indicated by the guinea pig ileum assay performed essentially as described by J. H. Sanner, Arch. int. Pharmacodyn., 180, 46 (1969). The compounds of this invention exhibited analgesic activity in mice, as indicated by the PBQ-writhing assay. Some of the compounds also exhibited anticonvulsant activity. The

SCHEME A

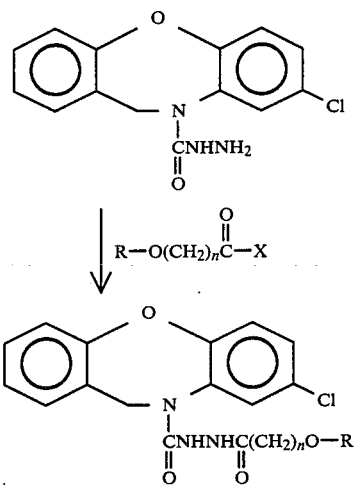

activities of the compounds of this invention illustrated in the examples were determined by the following methods.

Prostaglandin Antagonism Assay

Female albino guinea pigs weighing 200 to 500 grams were sacrificed by cervical dislocation. The ileum was quickly removed and placed in a modified Tyrode solution containing one-half the usual amount of magnesium ions. Segments of ileum about 2 cm long were cut and mounted in a 2- or 4-ml tissue bath containing the modified Tyrode solution, and the solution was maintained at 37° and aerated with a gaseous mixture of 95% oxygen and 5% carbon dioxide. Contractions were detected isotonically. Submaximal contractions were obtained by adjusting the dose of prostaglandin $E_2$ ($PGE_2$) added to the bath. Two control contractions were obtained at 3.5 minute intervals. A solution or suspension of the test compound in the bathing solution was then substituted for the original modified Tyrode solution. The test suspension was kept in constant contact with the tissue for the remainder of the experiment, except for brief periods to drain the bath in preparation for rinsing with fresh test suspension. Three more contractions were elicited for the $PGE_2$ agonist in the presence of the test compound without interrupting the time sequence. The last two sets of treated responses were compared with the two sets of control responses. (The first set of treated responses was not used for comparisons, being used only to maintain the timed sequence of injections during the period allowed for the tissue to become equilibrated with the antagonist.) A compound was rated active if the mean of contractions produced by the agonist was reduced 75% or more by the test compound.

PBO-Writhing Assay

Male Charles River albino mice (CD-1(ICR)BR) weighing 20 to 30 grams were used in this assay. Thirty minutes after subcutaneous or intagastric administration (0.1 ml per 10 g of body weight) or fifteen minutes after intracerebroventricular administration (5 mcl total volume), a 0.025% solution of phenylbenzoquinone (PBQ) was injected intraperitoneally (0.1 ml per 10 g of body weight). Five minutes later each mouse was placed in a glass beaker and the number of writhes occurring in the next ten minutes was counted. (A writhe consists of dorsoflexion of the back, extension of the hindlimbs, and strong contraction of the abdominal musculature.) The test compound was considered to have produced analgesia in a mouse if the number of writhes elicited by PBQ was equal to or less than one-half the median number of writhes recorded for the saline-treated control group of mice that day. Results were expressed as the number of mice out of a possible ten in which the test compound produced analgesia. If the initial screening dose of 10 mg/kg inhibited writhing in greater than six of ten mice, the effect of additional doses of the compound on the writhing response was evaluated and an $ED_{50}$ was calculated.

By virtue of their analgesic activity, the compounds of Formula I are useful in treating pain in mammals. A physician or veterinarian of ordinary skill can readily determine whether a subject is in pain. Regardless of the route of administration selected, the compounds of the present invention are formulated into pharmaceutically acceptable dosage forms by conventional methods known to those skilled in the art. Moreover, the compounds may be used in a suitable hydrated form.

The compounds can be administered in such oral dosage forms as tablets, capsules, pills, powders, granules, elixirs, or syrups. They may also be administered intravascularly, intraperitoneally, subcutaneously, intramuscularly, or topically, using forms known to the pharmaceutical art. In general, the preferred form of administration is oral. An effective but non-toxic quantity of the compound is employed in treatment. The dosage regimen for treating pain with the compounds of this invention is selected in accordance with a variety of factors, including the type, age, weight, sex, and medical condition of the patient; and the severity of the pain; the route of administration and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 0.1 to 100 mg/kg, preferably in the range of about 0.5 to 15 mg/kg.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium suflate, mannitol, and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents, and coloring agents can also be incorporated in the mixture.

Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

The following preparations and examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

PREPARATION OF STARTING MATERIALS AND INTERMEDIATES

Preparation 1 3-oxaheptanoic acid

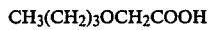
$CH_3(CH_2)_3OCH_2COOH$

Sodium metal (16 g) was added to 92.5 ml of butanol and heated at reflux under nitrogen. After the sodium had reacted, chloroacetic acid (32.9 g) in 40 ml of butanol was added dropwise and then heated at reflux for twenty hours. The mixture, upon cooling to room temperature, was added to 1300 ml of water and extracted four times with 250-ml portions of diethyl ether. The aqueous phase was acidified to about pH 2 with aqueous hydrochloric acid and again extracted four times with 250-ml portions of diethyl ether. The organic extracts were combined and dried over sodium sulfate, filtered, and concentrated in vacuo. Distillation afforded the title compound as an oil. Structure assignment was supported by the proton nmr spectrum.

Preparation 2 3-oxaheptanoyl chloride

$CH_3(CH_2)_3OCH_2CO-Cl$

To a solution of 4.5 g of the title product of Preparation 1 in 20 ml of toluene under nitrogen was added 5.9 ml of oxalyl chloride in four portions. The solution was stirred at room temperature for about twenty hours and then concentrated in vacuo to the oily title compound, which was used in subsequent reactions without further purification or characterization.

Preparation 3 5-oxahexanoic acid

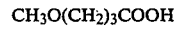
$CH_3O(CH_2)_3COOH$

A mixture of 86 g of gamma-butyrolactone in 1 liter of 2N aqueous sodium hydroxide was stirred for about sixty hours and then heated at reflux for about three hours. The mixture, upon cooling to room temperature, was extracted three times with 300-ml portions of diethyl ether. The aqueous phase was concentrated to dryness in vacuo and the residue was redissolved in about 140 ml of 40% aqueous sodium hydroxide. To this mixture was added 50 ml of dimethylsulfate and an additional 50 ml of 40% aqueous sodium hydroxide. The addition of dimethylsulfate and 40% sodium hydroxide was repeated twice more. The mixture was slowly heated to 90°, cooled to room temperature, acidified to about pH 2 with sulfuric acid, and extracted five times with 400-ml portions of diethyl ether. The organic extracts were combined, washed three times with 200-ml portions of water, dried over sodium sulfate, filtered, and concentrated in vacuo. Distillation afforded the title compound as an oil. Structure assignment was supported by the proton nmr spectrum.

Preparation 4 5-oxahexanoyl chloride

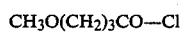
$CH_3O(CH_2)_3CO-Cl$

The title compound was prepared by the method of Preparation 2 using the title product of Preparation 3 instead of the title product of Preparation 1.

Preparation 5 3,6-dioxaheptanoic acid

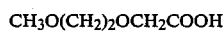
$CH_3O(CH_2)_2OCH_2COOH$

The title compound was prepared by the method of Preparation 1 using 176 g of 2-methoxyethanol instead of butanol. Structure assignment was supported by the proton nmr spectrum.

Preparation 6 3,6-dioxaheptanoyl chloride

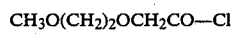
$CH_3O(CH_2)_2OCH_2CO-Cl$

The title compound was prepared by the method of Preparation 2 using the title product of Preparation 5 instead of the title product of Preparation 1.

DESCRIPTION OF THE EMBODIMENTS

Example 1

8-chlorodibenz[b,f][1,4]oxazepine-10(11H)-carboxylic acid, 2-(butoxyacetyl)hydrazide

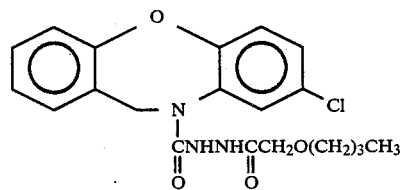

To a stirred mixture of 2.9 g of 8-chloro-10,11-dihydrodibenz[b,f][1,4]oxazepine-10-carboxylic acid hydrazide (see U.S. Pat. No. 3,534,019) and 2.68 ml of triethylamine in 50 ml of cold (0°) dichloromethane was slowly added 2.9 g of the title product of Preparation 2. The mixture was stirred for twenty hours at room temperature. The solution was then washed three times with 50-ml portions of water, dried over sodium sulfate, filtered, and concentrated in vacuo to give the title compound, m.p. 93°–97°.

Analysis Calcd. for $C_{20}H_{22}N_3O_4Cl$: C, 59.48, H, 5.49; N, 10.39. Found: C, 59.22; H, 5.52; N. 10.29.

Example 2

8-chlorodibenz[b,f][1,4]oxazepine-10(11H)-carboxylic acid, 2-(4-methoxy-1-oxobutyl)hydrazide

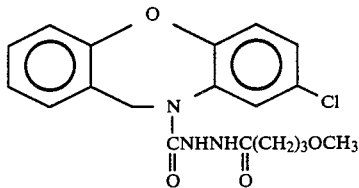

The title compound, m.p. 142°–144°, was prepared by the method of Example 1 using the title product of Preparation 4 instead of the title product of Preparation 2.

Analysis Calcd. for $C_{19}H_{20}H_3O_4Cl$: C, 58.53; H, 5.17; N, 10.78. Found: C, 58,52; H, 5.19; N, 10.84.

Example 3

8-chlorodibenz[b,f][1,4]oxazepine-10-(11H)-carboxylic acid, 2-(methoxyacetyl)hydrazide

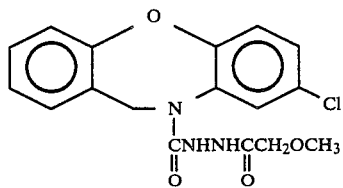

The title compound, m.p. 167°–169°, was prepared by the method of Example 1 using methoxyacetyl chloride instead of the title product of Preparation 2.

Analysis Calcd. for $C_{17}H_{16}N_3O_4Cl$: C, 56.43; H, 4.46; N, 11.62. Found: C, 56.60, H, 4.48; N, 11.76.

Example 4

8-chlorodibenz[b,f][1,4]oxazepine-10(11H)-carboxylic acid, 2-[(2-methoxyethoxy)acetyl]hydrazide

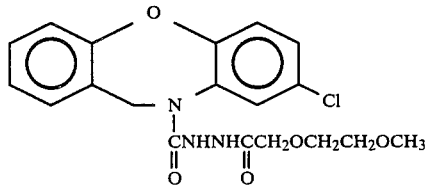

The title compound was prepared by the general method described in Example 1 using the title product of Preparation 6 instead of the title product of Preparation 2. Instead of a simple extraction, purification was effected by chromatography on silica gel using hexane containing increasing amounts of ethyl acetate as eluent.

Analysis Calcd. for $C_{19}H_{20}N_3O_5Cl$: C, 56.23; H, 4.98; N, 10.36. Found: C, 55.87; H, 4.88; N, 10.32.

What is claimed is:
1. A compound of the formula:

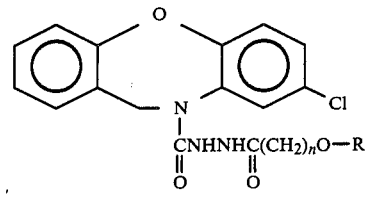

wherein R is:
(a) alkyl containing from 1 to 6 carbon atoms, inclusive; or
(b) alkoxyalkyl containing from 2 to 6 carbon atoms, inclusive; and
wherein n is an integer of 1 to 4, inclusive.

2. A compound according to claim 1 wherein R is alkyl containing from 1 to 6 carbon atoms, inclusive.

3. A compound according to claim 2, which is 8-chlorodibenz[b,f][1,4]oxazepine-10-(11H)-carboxylic acid, 2-(methoxyacetyl)hydrazide.

4. A compound according to claim 2, which is 8-chlorodibenz[b,f][1,4]oxazepine-10-(11H)-carboxylic acid, 2-(butoxyacetyl)hydrazide.

5. A compound according to claim 2, which is 8-chlorodibenz[b,f][1,4]oxazepine-10(11H)-carboxylic acid, 2-(4-methoxy-1-oxobutyl)hydrazide.

6. A compound according to claim 1 wherein R is alkoxyalkyl containing from 2 to 6 carbon atoms, inclusive.

7. A compound according to claim 6, which is 8-chlorodibenz[b,f][1,4]oxazepine-10-(11H)-carboxylic acid, 2-[(2-methoxyethoxy)acetyl]hydrazide.

8. A pharmaceutical composition comprising at least one compound according to claim 1, together with one or more non-toxic pharmaceutically acceptable carriers.

9. A pharmaceutical composition according to claim 8 wherein said compound is 8-chlorodibenz[b,f][1,4]oxazepine-10(11H)-carboxylic acid, 2-(methoxyacetyl)hydrazide.

10. A pharmaceutical composition according to claim 8 wherein said compound is 8-chlorodibenz[b,f][1,4]oxazepine-10(11H)-carboxylic acid, 2-(butoxyacetyl)hydrazide.

11. A pharmaceutical composition according to claim 8 wherein said compound is 8-chlorodibenz[b,f][1,4]oxazepine-10(11H)-carboxylic acid, 2-(4-methoxy-1-oxobutyl)hydrazide.

12. A pharmaceutical composition according to claim 8 wherein said compound is 8-chlorodibenz[b,f][1,4]oxazepine-10(11H)-carboxylic acid, 2-[(2-methoxyethoxy)acetyl]hydrazide.

13. A method for treating pain in mammals comprising administering a therapeutically effective amount of at least one compound of claim 1 to a mammal in need of such treatment.

14. A method according to claim 13 wherein said compound is 8-chlorodibenz[b,f][1,4]oxazepine-10-(11H)-carboxylic acid, 2-(methoxyacetyl)hydrazide.

15. A method according to claim 13 wherein said compound is 8-chlorodibenz[b,f][1,4]oxazepine-10(11H)-carboxylic acid, 2-(butoxyacetyl)hydrazide.

16. A method according to claim 13 wherein said compound is 8-chlorodibenz[b,f][1,4]oxazepine-10-(11H)-carboxylic acid, 2-(4-methoxy-1-oxobutyl)hydrazide.

17. A method according to claim 13 wherein said compound is 8-chlorodibenz[b,f][1,4]oxazepine-10(11H)-carboxylic acid, 2-[(2-methoxyethoxy)acetyl]hydrazide.

* * * * *